United States Patent [19]

Samulski et al.

[11] Patent Number: 5,478,745
[45] Date of Patent: Dec. 26, 1995

[54] RECOMBINANT VIRAL VECTOR SYSTEM

[75] Inventors: Richard J. Samulski; Xiao Xiao, both of Pittsburgh, Pa.

[73] Assignee: University of Pittsburgh, Pittsburgh, Pa.

[21] Appl. No.: 989,841

[22] Filed: Dec. 4, 1992

[51] Int. Cl.⁶ ............................ C12N 15/86; C12N 15/11
[52] U.S. Cl. .................. 435/320.1; 435/69.1; 435/172.3; 536/23.1; 536/24.1
[58] Field of Search .......................... 435/320.1, 69.1, 435/172.3, 235.1; 536/23.1, 24.1, 24.2

[56] References Cited

U.S. PATENT DOCUMENTS 4,797,368  1/1989  Carter et al. ........................ 435/320.1
5,139,941  8/1992  Muzyczka et al. ................... 435/172.3

OTHER PUBLICATIONS

Cheung, A. K. et al., 1980, "Integration of the Adeno–Associated Virus Genome into Cellular DNA in Latently Infected Human Detroit 6 Cells" J. Virology 33:739–748.
Berns, K. I. et al., 1982, "Adeno–Associated Virus Latent Infection" in Virus Persistence, eds. Mahey et al. (Cambridge University Press) pp. 249–265.
Samulski, R. J. et al., 1982, "Cloning of Adeno–Associated Virus Into pBR322: Rescue of Intact Virus From the Recombinant Plasmid in Human Cells", Proc. Natl. Acad. Sci. U.S.A. 79:2077–2081.
Miller A. D., 1990, "Retrovirus Packaging Cells" Human Gene Therapy 1:5–14.
Kotin, R. M. et al., 1990, "Targeted Integration by Adeno–Associated Virus", Proc. Natl. Acad. Sci. U.S.A. 87:2211–2215.
Samulski, R. J. et al., 1991, "Targeted Integration of Adeno–Associated Virus (AAV) Into Human Chromosome 19" The EMBO J. 10:3941–3950.
Muzyczka, N., 1992, "Use of Adeno–Associated Virus as a General Transduction Vector for Mammalian Cells" Current Topics in Microbiology & Immunology 158:97–129.

Primary Examiner—Richard A. Schwartz
Assistant Examiner—David Guzo
Attorney, Agent, or Firm—Pennie & Edmonds

[57] ABSTRACT

The present invention relates to a system for replication and encapsidation of recombinant DNA fragments into virus particles comprised of adenovirus associated viral (AAV) capsid proteins. The invention provides a means of obtaining recombinant viral stocks that may be used to treat patients suffering from genetic diseases.

5 Claims, 11 Drawing Sheets

```
5 - AGGAACCCCT AGTGATGGAG TTGGCCACTC CCTCTCTGCG CGCTCGCTCG CTCACTGAGG    60
    CCGGGCGACC AAAGGTCGCC CGACGCCCGG GCTTTGCCCG GGCGGCCTCA GTGAGCGAGC   120
    GAGCGCGCAG AGAGGGAGTG GCCAACTCCA TCACTAGGGG TTCCT - 3'              165
```

FIG.1A

5'- AGGAACCCCT AGTGATGGAG TTGGCCACTC CCTCTCTGCG CGCTCGCTCG CTCACTGAGG  60
CCGGGCGACC AAAGGTCGCC CGACGCCCGG GCTTTGCCCG GGCGGCCTCA GTGAGCGAGC 120
GAGCGCGCAG AGAGGGAGTG GCCAACTCCA TCACTAGGGG TTCCT -3' 165

FIG.9

5'- CCCTGTATCC TAAATCAAAT ATCGGACAAG CAGTGTCTGT TATAACAAAA AATCGATTTA  60
ATAGACACAC CAACAGCATG GTTTTTATGT GTGCGATAAT TTATAATATT TCGGACAGGG -3' 120

FIG.10

RECOMBINANT VIRAL VECTOR SYSTEM

INTRODUCTION

The present invention relates to a system for replication and encapsidation of recombinant DNA fragments into virus particles comprised of adenovirus associated viral (AAV) capsid proteins. The invention provides a means of obtaining recombinant viral stocks that may be used to treat patients suffering from genetic diseases.

BACKGROUND OF THE INVENTION

The most well studied models for gene therapy involve gene transfer using recombinant pathogenic viruses to express new genetic information in order to correct disease phenotypes. Until recently, the most widely researched viral vectors for use in gene therapy were the retroviruses (Miller, A.D., 1990, Human Gene Ther. 1:5–14). A number of difficulties are associated with retroviral use, including the random integration of retroviruses into the host genome which may lead to insertional mutagenesis, or the inadvertent activation of protoncogene expression due to the promoter activity associated with retroviral LTRs (long terminal repeats). Recent evidence using retrovirus vectors in non-human primates has resulted in T cell lymphomas. Efforts in the field of gene therapy have more recently concentrated on the development of viral vectors lacking these particular characteristics.

AAV can assume two pathways upon infection into the host cell. In the presence of helper virus, AAV will enter the lytic cycle whereby the viral genome is transcribed, replicated, and encapsidated into newly formed viral particles. In the absence of helper virus function, the AAV genome will integrate as a provirus into a specific region of the host cell genome through recombination between the AAV termini and host cell sequences (Cheung, A. et al., 1980, J. Virol. 33:739–748; Berns, K. I. et al., 1982, in Virus Persistence, eds. Mahey, B. W. J., et al. (Cambridge Univ. Press, Cambridge), pp. 249–265).

Characterization of the proviral integration site and analysis of flanking cellular sequences indicates specific targeting of AAV viral DNA into the long arm of human chromosome 19 (Kotin, R. M. et al., 1990, Proc. Natl. Acad. Sci. U.S.A. 87:2211–2215; Samulski, R. J. et al., 1991, EMBO J. 10:3941–3950). This particular feature of AAV reduces the likelihood of insertional mutagenesis resulting from random integration of viral vector DNA into the coding region of a host gene. Furthermore, in contrast to the retroviral LTR sequences, the AAV ITR (inverted terminal repeat) sequences appear to be devoid of transcriptional regulatory elements, reducing the risk of insertional activation of protooncogenes.

The AAV genome is composed of a linear single stranded DNA molecule of 4680 nucleotides which contains major open reading frames coding for the Rep (replication) and Cap (capsid) proteins. Flanking the AAV coding regions are two 145 nucleotide inverted terminal (ITR) repeat sequences that contain palindromic sequences that can fold over to form hairpin structures that function as primers during initiation of DNA replication (FIG. 1). Furthermore, experimental observations indicated that the ITR sequences were needed for viral integration, rescue from the host genome and encapsidation of viral nucleic acid into mature virions [Muzyczka, N. 1992, Current Topics in Microbiology & Immunology. 158, 97–29].

Recent work with AAV has been facilitated by the discovery that AAV sequences cloned into prokaryotic vectors are infectious [Samulski, et al. 1982, Proc. Natl. Acad. Sci. U.S.A. 79:2077–2081]. When a plasmid containing intact AAV genome is transfected into cells in the presence of helper virus, AAV can be rescued out from the plasmid vector and enter the lytic pathway leading to production of mature virions. In the absence of helper virus the recombinant AAV vector will integrate into the host cell genome and remain as a provirus until the cell subsequently becomes infected with a helper virus.

SUMMARY OF THE INVENTION

The invention relates to a novel 165 basepair fragment of DNA which contains AAV ITR sequences and which can be synthesized in vitro and used to engineer expression vectors and/or vectors useful for genetic therapy. This 165 bp DNA sequence, herein referred to as the double-D sequence, is in a novel configuration not found to exist in wild type AAV.

The invention is based, in part, on the discovery of the ability of the double-D sequence to provide sufficient information, in cis, for converting a circular duplex DNA molecule into a linear replicating molecule with covalently closed ends, encapsidation into AAV virions, or integration into the host genome. The invention provides an in vivo system for replication and packaging of recombinant DNA fragments into mature virions. The resulting recombinant viral stocks afford a convenient and efficient means for transfer of genetic information into any cell or tissue of choice. The system may have applications in gene therapy where the desired goal is correction of a given genetic abnormality through expression of the normal complement of the defective gene.

The invention also relates to in vitro treatment of recombinant viral vectors and/or vectors useful for genetic therapy with bacterial gamma delta resolvase prior to transfection. Genetic engineering of resolvase recognition sequences into recombinant vectors creates the option of removing bacterial plasmid sequences which would normally be included as part of the linear, replicated, and encapsidated DNA molecule. Removal of these bacterial sequences, prior to replication and encapsidation, allows the maximum amount of space for insertion of foreign DNA sequences of interest into the expression vectors.

The invention is described by way of examples in which an AAV double-D fragment is amplified in a polymerase chain reaction (PCR) and inserted into a plasmid vector. A viral stock, containing the recombinant DNA encapsidated into mature virions, may be obtained by transfection of the expression vector into a host cell expressing helper functions.

BRIEF DESCRIPTION OF THE DRAWINGS

Figure 1A:
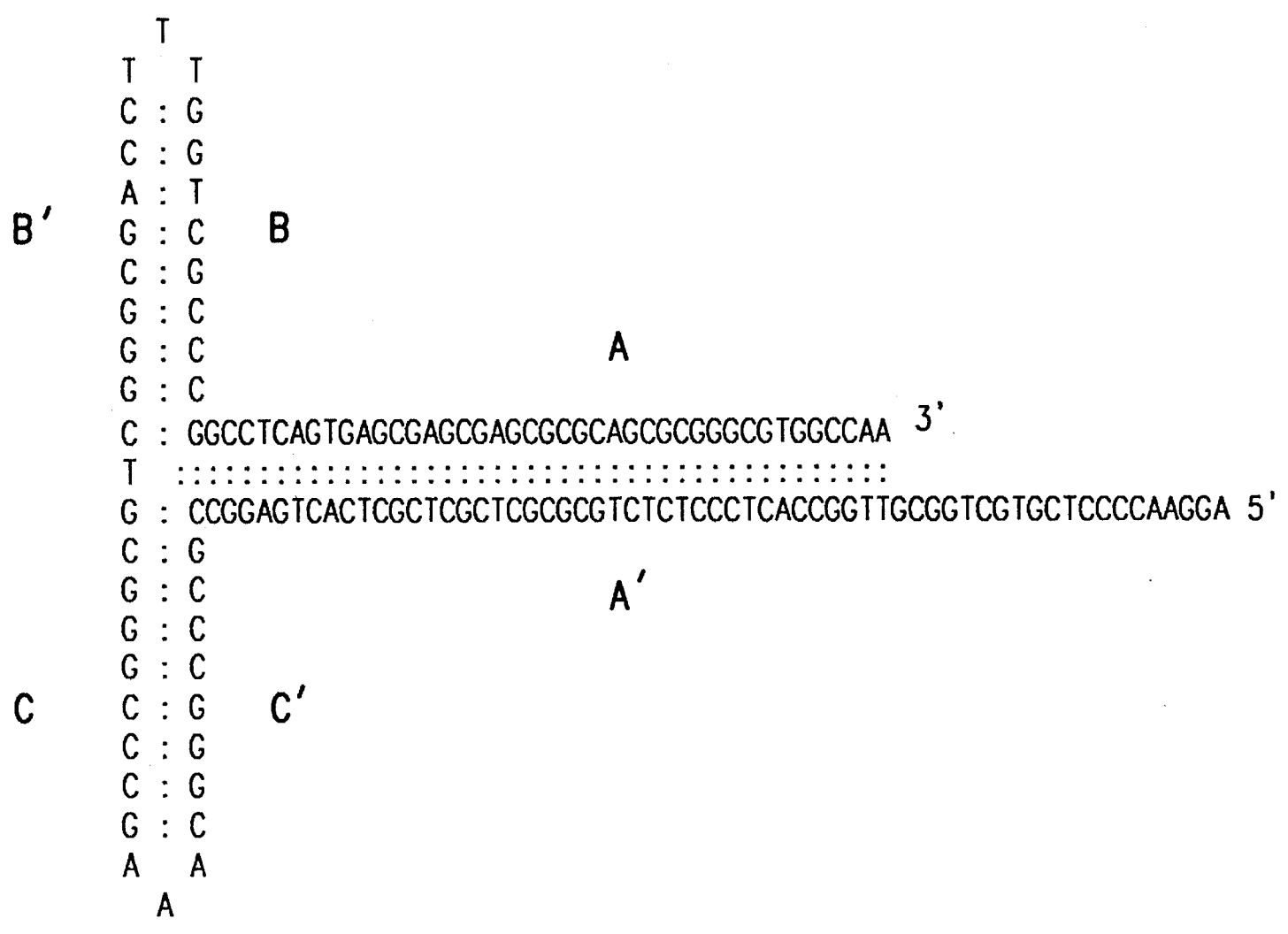

FIGS. 1A–1C. AAV rescue and replication mechanisms. (A) Inverted terminal repeats (ITR) may fold back through the base-pairing of A, A', B, B', C, C' sequences to form a T-shape structure (SEQ ID NO: 6). (B) Excision of infectious plasmid at the ITR sites yields two linear DNA fragments: AAV and the plasmid vector. (C) Predicted fragments generated from double D plasmid after rescue from plasmid circular form to linear with covalent closed ends.

FIG. 9. Double-D sequence (SEQ ID NO: 1).

FIG. 10. Bacterial Gamma Delta Resolvase recognition sequence (SEQ ID NO: 2).

DETAILED DESCRIPTION OF THE INVENTION

Figure 1B:
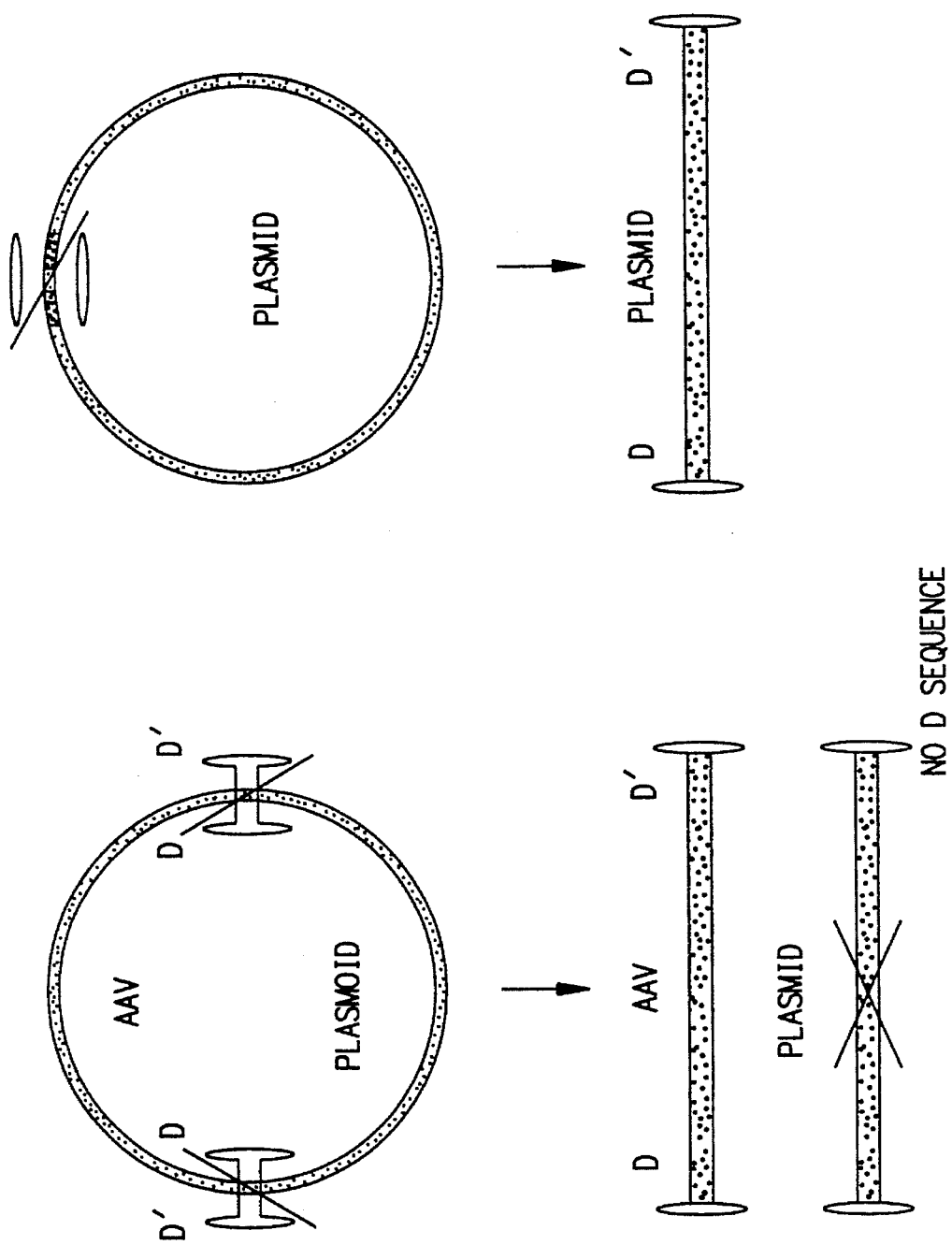

The present invention relates to the use of a novel modified AAV ITR nucleotide sequence, herein referred to as the double-D sequence. The invention is based in part on the synthesis of a double-D DNA fragment using PCR technology, and the demonstration that this fragment provides sufficient information in cis for replication and encapsidation of recombinant DNA fragments into mature AAV virions, or the specific integration of recombinant DNA into the host genome. The invention further relates to the use of the double-D DNA sequences in eukaryotic vectors and the use of these vectors for gene replacement therapies.

The double-D sequences may be genetically engineered into vectors designed to introduce and/or express a heterlogous gene of interest. For use in gene therapy, the heterlogolous gene of interest may represent the normal or wild-type version of a defective or mutant gene associated with a given genetic disease. The recombinant vectors, in addition to containing the coding region for the gene of interest and the double-D sequences, may contain other necessary regulatory elements such as promoter/enhancer elements, and translation and polyadenylation signals. The selection of promoter and enhancer regions will rely on the desired level and tissue specific expression of the gene of interest.

The transfection of recombinant vectors into a host cell line that provides helper virus function and supplies in trans the REP and CAP proteins allows one to obtain a recombinant virus stock (Muzyczka, N. 1992, Current Topics in Microbiology and Immunology 158:97–129). The resulting virus stock may then be used as a highly efficient means of delivery and transfer of new genetic information into targeted cells or tissues of choice.

5.1. The AAV Viral Sequences

The AAV genome consists of 4680 nucleotides containing two open reading frames that encode the REP (replication) and CAP (capsid) proteins. Located at both ends of the genome are 145 bp inverted terminal repeats (ITRs), which are unique in that they can not only basepair with each other, but also individually fold back on themselves through the basepairing of A, A', B, B', C, C' sequences to form a T-shaped structure for DNA replication when single stranded (FIG. 1A)(SEQ ID NO: 6).

When a plasmid containing an intact AAV genome is transfected into the adenovirus infected cells, AAV can be rescued or replicate out from the plasmid vector and enter the viral lytic cycle leading to production of mature virions. In addition, if the AAV coding region is deleted and replaced by heterologous DNA sequences, the recombinant AAV can still complete the viral lytic cycle provided the ITRs are intact and the REP and CAP proteins, or functional equivalents, are supplied in trans. However, if one of the two ITR sequences are deleted no viral DNA replication is observed indicating that both ITRs are required for AAV viability.

The invention is based, in part, on the discovery that the following 20 basepair D sequence (AGGAACCCCTAGT-GATGGAG) (SEQ ID NO: 5) present in the ITR sequence was required for viral replication. This was initially demonstrated by the inability of viral mutants with deleted D sequences to replicate their DNA Furthermore, during the replication of a terminal resolution site mutant, natural deletions were found to occur only towards the A sequence of the ITR and not towards the D end, suggesting a selection process for retention of D sequences.

Figure 7:
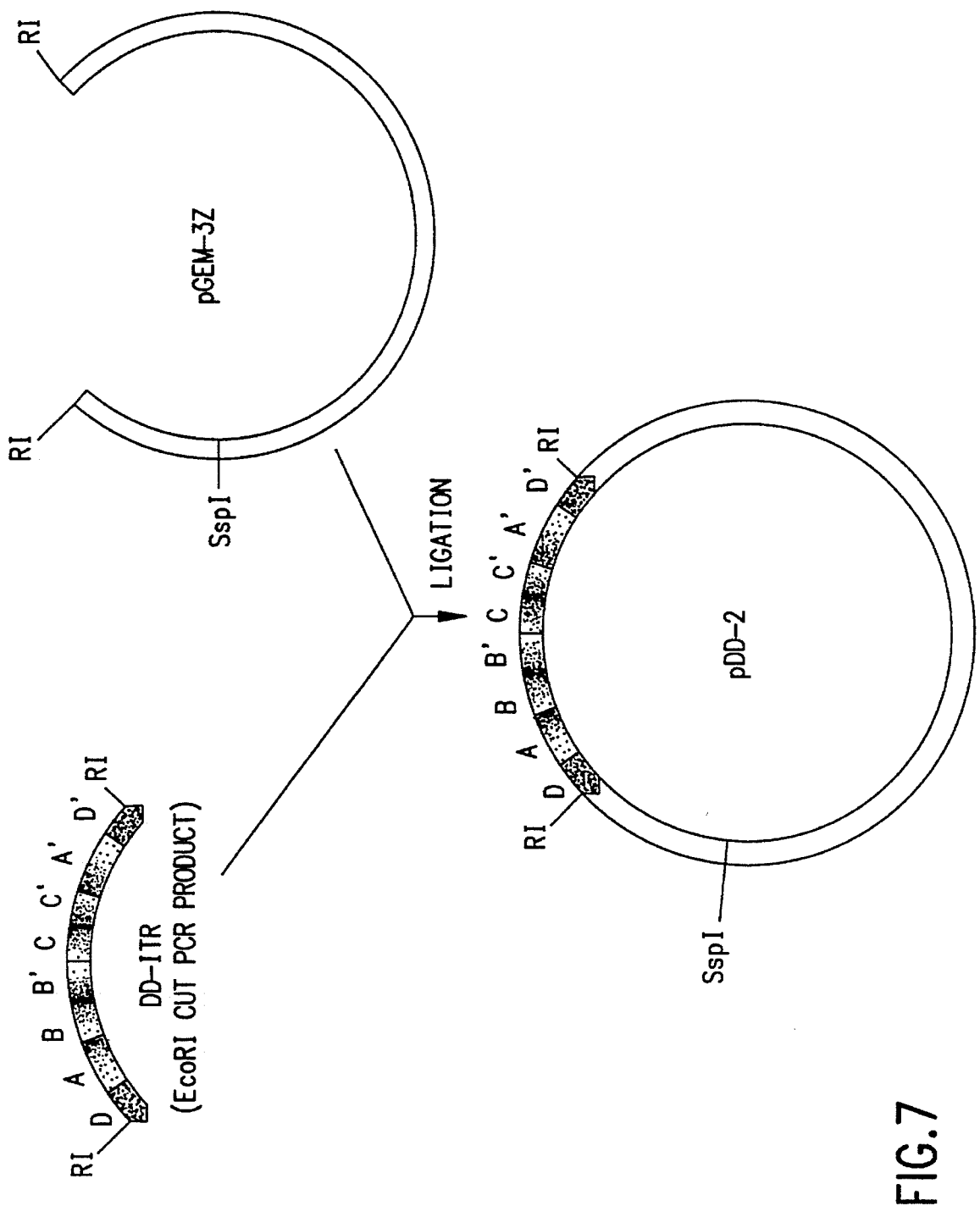
FIG. 7. Cloning of PCR-amplified and EcoRI cut double-D into EcoRI site of plasmid pGEM-3'Z.

In order to elucidate further the function of the D sequences, a novel modified terminal repeat structure was constructed containing a single 145 bp ITR sequence with an additional 20 bp D' sequence (FIG. 9) (SEQ ID NO: 1) (See Section 6.13, infra). The resulting 165 bp sequence has not been identified in any naturally occurring virus. Using AAV DNA as template and a single primer derived from the D sequence of the AAV ITR sequence plus 6bp of EcoRI recognition site on the 5' end, a polymerase chain reaction was performed that resulted in a DNA fragment comprised of an ITR flanked on either side by D or D' sequences as well as EcoRI sites. The PCR generated DNA fragment was cleaved by EcoRI to produce sticky end, and subsequently cloned into the EcoRI site of pGEM3Z (FIG. 7). A recombinant plasmid containing the double-D structure was transfected into cells to determine whether the double-D was able to function in replication, encapsidation, integration and rescue of recombinant DNA. Results from these experiments indicate that the novel double-D sequence is sufficient to carry out the functions normally required of two wild type ITRs during a lytic or latent AAV viral infection (See Section 6.2.3. and Section 6.2.4., infra).

5.2. Construction of Recombinant Vectors Comprised of AAV Viral Sequences and Heterologous Linked Sequences The double-D sequences (SEQ ID NO: 1) of the invention provide the necessary information required for directing the replication and encapsidation of recombinant DNA into mature virions. A DNA fragment containing a double-D nucleotide sequence may be obtained by any number of methods commonly used in the art. In a specific embodiment, described herein, a polymerase chain reaction (PCR) was used to obtain a double-D DNA fragment using AAV DNA as template and a primer derived from the D sequence of the AAV ITR. The rationale for this approach is based on the expected secondary structure of the natural ITR sequence. In the first round of the PCR reaction, the AAV viral IRT forms a hairpin structure and self-primes the elongation process to produce a long T-shaped hairpin structure containing D and D' on the stem. Upon denaturation, this DNA serves as template for a single-primed PCR reaction. Alternative methods for isolating a double-D DNA fragment, include but are not limited to chemically synthesizing the DNA sequence.

Altered nucleotide sequences which may be used in accordance with the invention include derivatives and analogs of the double-D sequence that are functionally equivalent in that they retain their ability to provide information, in cis, for replication, encapsidation, integration and rescue of recombinant DNA. In particular, double-D derivatives may contain additions, substitutions or deletions of nucleotide sequences but still retain biological function.

Standard recombinant DNA methods may be used for insertion of novel double-D sequences into eukaryotic expression vectors. These include in vitro recombinant DNA techniques, synthetic techniques and in vivo recombination/ genetic recombination. For example, the double-D DNA sequence may be amplified in a PCR reaction using oligonucleotide primers that add an appropriate restriction endonuclease recognition site onto each end of the amplified DNA fragment (See Section 6.1.3). Alternatively, any restriction site desired may be produced by ligating nucleotide sequences (linkers), comprising specific chemically synthesized oligonucleotides encoding restriction endonuclease recognition sequences, onto the termini of the amplified double-D fragment into an expression vector having complementary cohesive termini.

A variety of host recombinant vector systems may be utilized equally well by those skilled in the art. The recombinant vectors could contain bacterial plasmid sequences necessary for replication in *E. coli* or the cis acting double-D sequence could be ligated directly to the gene of interest. In addition, plasmids will contain DNA sequences coding for a heterologous gene of interest, inserted between the appropriate transcriptional/translational control sequences and polyadenylation signals. A variety of promoter/enhancer elements may be used depending on the level and tissue specific expression desired. Promoters produced by recombinant DNA or synthetic techniques may be used to provide for transcription of the inserted gene of interest. Specific initiation signals are also required for efficient translation of inserted protein coding Sequences. These sequences include the ATG initiation codon and adjacent sequences. In addition, polyadenlylation signals may be included to increase the stability of transcribed mRNA.

One potential drawback of the AAV viral vector system is the size limitation imposed by the inability of DNA fragments larger than 5 Kb to be packaged into mature virus particles. In any given expression vector, 2–3 Kb of DNA sequence derives from bacterial plasmid sequences which are required for propagation of plasmid in *E. coli*. These DNA sequences include origin of replication (ori) sequences and genes that confer resistance to antibiotics such as ampicillin and tetracycline. In effect, this leaves only 2 Kb of space for insertion of heterlogolous genes of interest.

The following particular, non-limiting embodiment of the invention addresses this size limitation problem. To increase the amount of space available for cloning of sequences of interest, a bacterial recombination system (gamma delta) may be used to resolve plasmids in such a manner that the majority of the bacterial plasmid DNA sequences will be recombined out of any given recombinant plasmid construct in vitro, thereby allowing for the maximum amount of space for insertion of foreign genes. The gamma delta resolvase sequences may be used in a variety of viral vector systems, not limited to AAV systems, as a general method for increasing the space available for insertion of foreign genes.

Figure 8:
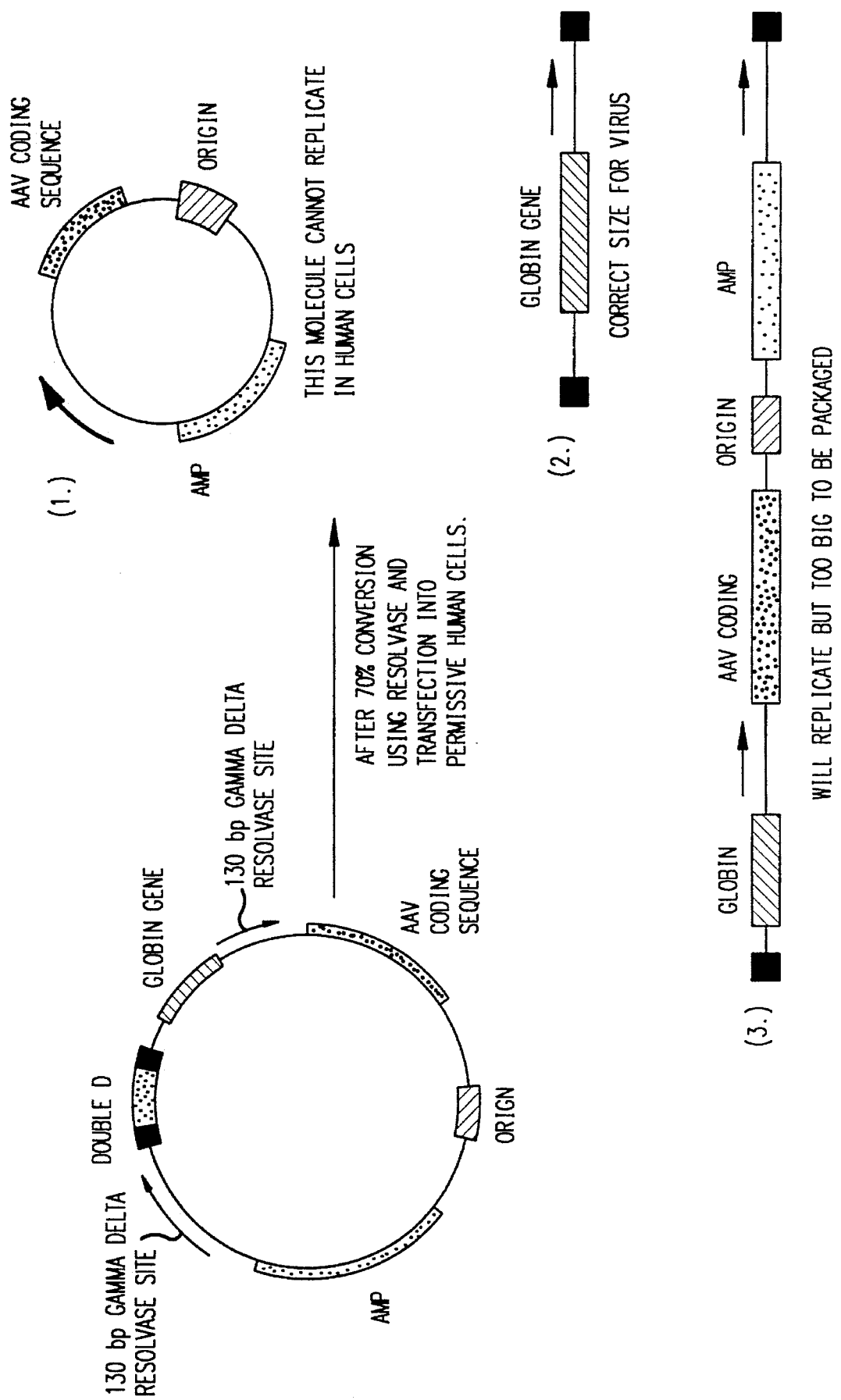
FIG. 8. In-vitro replication of parental plasmid containing resolvase sequences.

The parental double-D expression vector plasmid may be engineered to contain, in addition to the double-D sequence, two copies of the gamma delta resolution site (FIG. 10) (SEQ ID NO: 2) (120 basepairs) in the correct orientation so as to promote recombination when resolved in vitro with gamma delta resolvase enzyme. In the presence of gamma delta resolvase, the recombinant plasmid should be converted into two circular DNA molecules (FIG. 8). One plasmid molecule should contain the primary bacterial plasmid sequences along with a copy of the gamma delta resolution site. The other resolved plasmid molecule would be expected to contain the double-D cis acting sequences, one copy of a gamma delta resolution site and the coding region for the gene of interest. It is this plasmid molecule which will be converted, in the presence of helper virus and the viral REP and CAP proteins, into a linear replicating molecule which will then be encapsidated into mature viral particles.

Currently, a second plasmid is required to supply the CAP and REP proteins which are needed to convert circular plasmid molecules into replicating linear DNA fragments. In a further particular embodiment of the invention, plasmids containing the gamma delta resolution sites may be engineered to also contain the coding regions for the required viral REP and CAP functions. Normally the REP and CAP coding sequences would be excluded from the expression vector because they further limit the size of your insert. Using the in vitro recombination system, these coding regions may be included in the plasmid construct, since they will be recombined out during resolution through the two gamma delta resolution sites by the resolvase enzyme (FIG. 8). The products are two concatenate DNA molecules.

Because the in vitro gamma delta reaction is a linear reaction, the amount of resolved molecules may be controlled in the in vitro resolving reaction to generate desired ratios of parental plasmid to resolved circles. The mixture of plasmids can then be transfected into the host cell. This introduces one circular molecule containing the AAV REP and CAP genes required in trans for a productive replication, and the other circular molecule contains the double-D ITR sequences and the gene of interest. The double-D circular molecule may be replicated into a linear DNA molecule which may subsequently be encapsidated into viral particles by the trans factors introduced on the REP/CAP circular plasmid.

The present invention further provides for the analogous use of the above-described gamma delta resolvase system to first propagate plasmids that comprise (i) a recombinant viral vector sequence comprising a gene of interest, (ii) viral genes providing helper functions, and (iii) two gamma delta resolvase recognition sequences flanking the viral vector sequence (SEQ ID NO: 2) and, second, to separate recombinant viral vector sequences comprising the gene of interest from the remaining plasmid sequence using resolvase enzyme. According to these methods, the virus from which the vector and helper functions are derived may be any suitable virus including but not limited to AAV, a retrovirus, adenovirus, or herpes virus. In preferred embodiments the viral vector portion of the plasmid comprises the double-D sequence or, alternatively, both AAV ITR's. In general, the viral vector protein comprises sequences necessary for encapsidation and transcription of the gene of interest.

5.3. Production of Recombinant Virus Stocks

The invention relates to a method for replicating and encapsidating a recombinant DNA molecule into an AAV particle which comprises culturing a eukaryotic cell containing helper virus, recombinant DNA encoding AAV REP and CAP proteins, and a recombinant nucleic acid containing a DNA sequence of interest and the 165 base pair double-D sequence.

To generate recombinant viral stocks, the double-D recombinant expression vector plasmid may be transfected into a host cell line that is able to provide helper virus function, and supply in trans AAV REP and CAP proteins. The REP and CAP proteins are required for replication and encapsidation of the linear recombinant DNA into mature viral particles.

The REP and CAP proteins may be supplied in trans by transfection of the host cell line with a recombinant plasmid that is capable of coding for each of the proteins. DNA transfections may be carried out using methods well known to those skilled in the art. These may include DNA transfection by lipofection, electroporation or calcium phosphate precipitation [Ausubel, et al., 1989, in Current Protocols for Molecular Biology,]. The plasmid is transfected into the host cell line with the intention of either transiently or stably expressing the REP and CAP proteins. In a specific embodiment, described in Section 6.1., the plasmid pAAV/AD containing the AAV coding regions, was transfected into a host cell for the purpose of expressing the REP and CAP proteins.

In another embodiment, the double-D expression vector may be engineered to directly express the REP and CAP proteins. In this case, it is also important to include the gamma delta resolvase sequences in the plasmid vector, so that the REP and CAP coding regions may be recombined out during an in vitro resolvase reaction so as not to impose a size limitation on the insert of foreign DNA.

In addition to expressing the viral REP and CAP proteins, the host cell lines must be able to provide helper virus function. Both adenovirus and herpes simplex virus may serve as helper viruses for replication of DNA fragments containing the double-D sequences. Any host cell permissive for infection by either of these two viruses or any virus that acts as a helper virus for AAV, may be used in the practice of the invention. The multiplicity of infection (MOI) and the duration of the infection time will depend on the type of virus used and the cell line employed.

In a specific embodiment, described herein, 293 cells which had previously been transfected with a recombinant double-D expression vector, were infected with Ad5 at a MOI of 10. Forty-eight hours later the cells were frozen and thawed three times, and incubated for one hour at 56° C. to inactivate the adenovirus. The resulting cell lysate contains recombinant viral particles that may be used to infect cells or tissue of choice.

5.4. Uses of Recombinant Vectors

There are numerous human genetic disorders from which patients suffer, which include diseases such as sickle cell anemia, thalassemias, Lesch-Nyhan disease and cystic fibrosis. Current therapies do little to alleviate the symptoms associated with these diseases and efforts are currently underway to develop new methods for the treatment of genetic diseases.

Recent advances in molecular techniques have made it possible to isolate the normal complement of a given defective gene and this has led to the concept of "gene therapy", and the acceptance of gene therapy as a feasible means of treatment for those suffering from genetic disorders. Until recently, retroviruses were the most widely researched viral vectors for use in gene therapy. Unfortunately, a number of difficulties are associated with retroviral use which include the random integration of retroviral DNA into the host chromosome leading to insertional mutagenesis or activation of protooncogene expression.

AAV vectors provide a viable alternative to the retroviral systems for use in gene therapy. The nonrandom integration of AAV into the host chromosome and the lack of transcriptional activity associated with the ITR structures indicate that AAV may be particularly beneficial for treatment of genetic disorders.

The double-D expression vectors, containing a gene of interest and described herein, may be useful for therapeutic treatment of genetic disorders. The gene of interest may be the wild type complement of any mutated or defective gene and may be inserted into the double-D recombinant vectors so that its expression is controlled by its natural promoter (e.g., so that expression is regulated normally) or by a heterologous promoter. A recombinant viral stock may be generated by transfection of the double-D plasmid into a suitable host cell line that first allows for conversion of a circular duplex molecule into a linear DNA molecule covalently closed at both ends. This then permits replication and encapsidation of recombinant DNA into mature viral particles. The resulting viral stocks contain infectious viral particles that may then be used to infect tissue or cells affected by the genetic defect.

EXAMPLE

A Novel 165 Base Pair Terminal Repeat is the Only cis-Element Required for Adeno-Associated Virus Life Cycle The subsection below describes the synthesis and functional characterization of the double-D ITR sequence.

6.1. Materials and Methods 6.1.1. DNA Transfection

Human cell line 293 was maintained in DMEM (Dulbecco modified Eagle medium, GIBCO) WITH 10% FCS (fetal calf serum, HyClone). Transfection of plasmid DNA was done by lipofectin (BRL) method as described by the manufacturer. Briefly, cells in a 6-cm dish were washed twice with DMEM and infected with Adenovirus 5 at 10 moi (multiplicity of infection) in 1 ml Opti-MEM (GIBCO) for 1 hr. Then 5 ug plasmid DNA was incubated with 50 ul of lipofectin (BRL) at room temperature for 10 min, mixed with 2 ml of Opti-MEM and added to the Adenovirus infected cells. After incubation for 12 hrs., the cells were fed with 3 ml of DMEM containing 4% FCS and incubated for an additional 36 hours.

6.1.2. Southern Hybridization

Low molecular weight DNA from transfected cells was extracted as described by Hirt (Hirt, B. 1967, J. Mol. Biol. 26:365–369). The DNA was digested by restriction enzymes (New England BioLab), separated on an agarose gel, then transferred onto the Genescreen plus Nylon membrane (DuPont). Hybridization with $^{32}P$ labeled plasmid DNA was carried out as recommended by the manufacturer. Hybridization with r- $^{32}P$-ATP end-labeled ITR oligonucleotide probe A-1 (5'TTGGCCACTCCCTCTCTGCG3') (SEQ ID NO: 4), derived from A region of ITR, kindly provided by N. Muzyczka) was performed as follows: the membrane was prehybridized in 10 ml solution containing 5X SSC, 10X Denhardt's solution, 10% dextran sulfate and 5% SDS at 60° C. for at least 1 hr. 25 ng of $^{32}p$ end labeled oligo-probe and 200 ug heat-denatured salmon sperm DNA in 0.5 ml $H_2O$ were added. Hybridization was continued at 60° C. overnight. The membrane was washed twice in 3X SSC and 5% SDS at 60° C. for 30 minutes and once in 0.2X SSC at room temperature for 10 minutes.

6.1.3. PCR and Construction of ITR Plasmid

Low molecular weight DNA from AAV and Ad5 infected cells was used as template for the PCR reaction with a single primer derived from D-sequence of AAV. The PCR was performed at 94° C. 1 min., 45° C. 30 seconds and 72° C. 1 min. for 35 cycles in a 50 ul reaction solution containing 20 mM Tris-HCl (pH8.8), 1.5 mM MgCl, 50 mM KCl, 2.5% formamide, 100 uM dATP, dCTP and dTTP, 75 uM 7-deazo-dGTP, 25 uM dGTP, 1.5U AmpliTaq (Perkin Elmer Cetus), 1 ng AAV DNA and 100 pmole primer TR-1 (5'-GGAATTCAGGAACCCCTAGTGATGG3-3') (SEQ ID NO: 3). The PCR product was purified by agarose gel electrophoresis, cut with EcoRI and ligated with an EcoRI cut and dephosphorylated pGEM 3Z plasmid (Promega). The ligated plasmid was transformed into *E. coli* Sure strain (Stratagene). Positive clones named pDD's were screened for the presence of double-D terminal repeat and confirmed by dideoxy-sequencing with 7-deazo-dGTP substituted for dGTP (Sanger, F. et al., 1977, Proc. Natl. Acad. Sci. U.S.A. 74:5463–5467). Subsequently, a neogene was cloned into the SalI site of pDD-2 resulting in the plasmid pDD-neo.

6.1.4. Cloning of Neo-Resistant Cell Lines

Ad5 infected 293 cells were cotransfected with pDD-neo and pAAV/Ad [Samulski, et al., 1989. J. Virol. 63:3822–3828] for 48 hrs. The cells were frozen and thawed three times and then incubated at 56° C. for 1 hour to inactivate the Ad5 virus. The cell lysate containing the DD-neo recombinant AAV virus was used to infect the human cell line Detroit 6. The cells were inoculated for 24 hours, then selected with G418 at 400 ug/ml to obtain neo-resistant clones. Various clones were superinfected with wild-type AAV and Ad5 at a MOI of 10 to rescue the latent neo-AAV.

6.2. Results

6.2.1. Construction of ITR with Double-D Sequence

The Polymerase Chain Reaction (PCR) was used to construct the inverted terminal repeat with a D' sequence added to the other end. The rationale is based on the T-shape structure of the ITR. In the first round of PCR reaction, the AAV viral IRT will self-prime the elongation to produce a long T-shaped hairpin structure containing D and D' on the stem. Upon denaturation, this DNA can serve as template for single-primed PCR.

Figure 2:
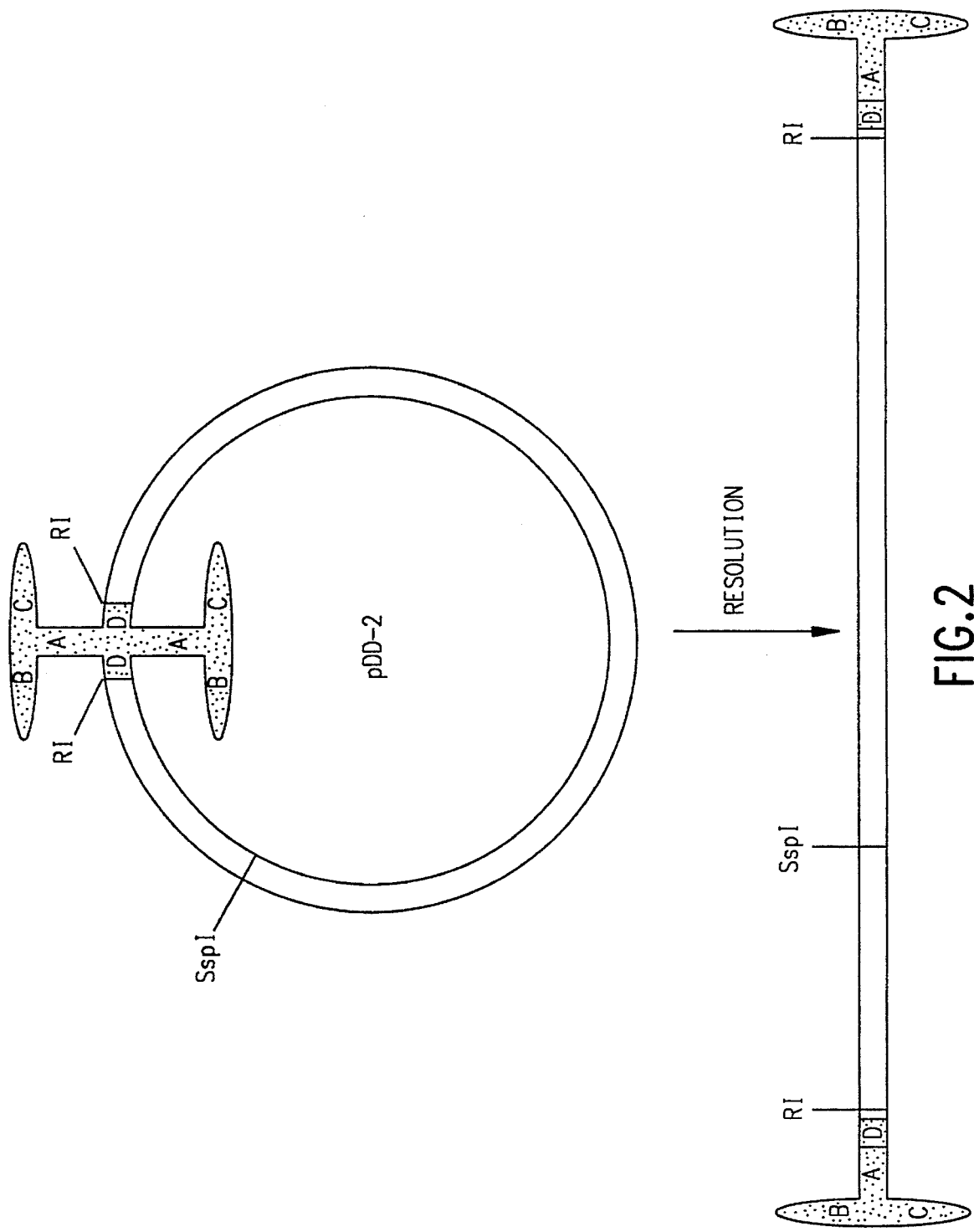
FIG. 2. Rescue Intermediate from circular double-D plasmid.

Owing to the high GC content and the strong palindromic structure in the ITR region, several strategies such as 7-deazo-dGTP, 2.5% formamide, and high concentration of primer were utilized to tackle the PCR problems and yield sufficient desired PCR product. For the convenience of cloning, an EcoRI recognition sequence was attached to the 5' of the primer so that the PCR product can be cut by EcoRI and easily cloned into the polylinker of pGEM 3Z. Due to the instability of the ITR in bacteria host, the recombinant plasmid was transformed into an *E. coli* SURE strain (Stratagene) in which the ITR was rather stable. By using the above strategy, we obtained numerous positive clones. Some clones were characterized by restriction digestion and sequencing. One of the clones is shown in FIG. 2 bearing an insert of D'ABB'CC'A'D in the EcoRI site of the pGEM 3Z. This plasmid was named pDD-2 and was used in the following transfection experiments.

6.2.2. pDD-2 Replication is Dependent on REP

Figure 3A:
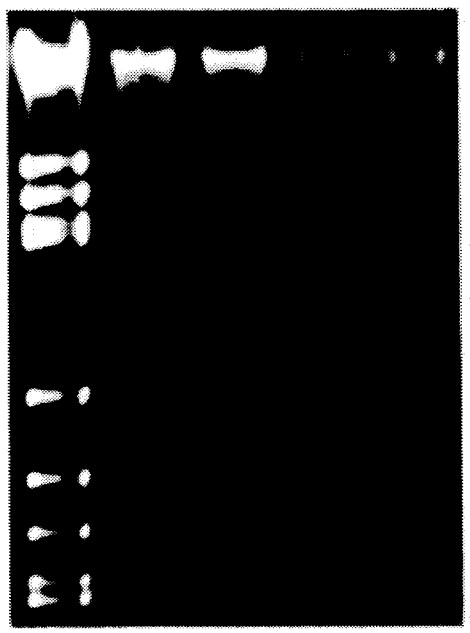
FIG. 3. Replication assay for the plasmid containing the double-D fragment. Plasmid pDD-2 was transfected into Ad5 infected 293 cells with or without cotransfection of the helper plasmid pAAV/Ad. Low molecular weight DNA was extracted 48 hrs. post infection and separated on a 1% agarose gel with or without DpnI digestion. (A) Ethidium bromide staining of the gel. (B) Southern blot with $^{32}$p labeled plasmid pGEM 3z probe.
Figure 3B:
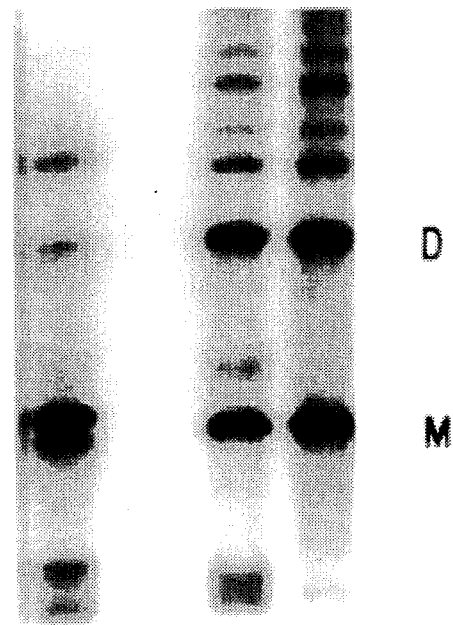

In order to assay the capability for replication, Plasmid pDD-2 was transfected into Ad5 infected 293 cells with or without cotransfection of a helper plasmid pAAV/Ad, which contains functional REP and CAP genes but without the ITR, so that it can not replicate. Due to the lack of functional origins this molecule can only supply REP and CAP proteins in trans. Post transfection for 48 hours, the plasmid DNA was extracted and separated on 1% agarose gel with or without DpnI digestion. DpnI only digests the input methylated plasmid DNA while leaving the replicated (demethylated) DNA intact. The results demonstrated that in the absence of the helper plasmid, pDD-2 plasmid did not replicate therefore the DNA is completely DpnI sensitive (FIG. 3, lane 1 and 2). However, in the presence of the helper plasmid, pDD-2 replicated very efficiently as evidenced by the resistance to DpnI digestion and the existence of monomer and dimer molecules: the typical AAV replication pattern (FIG. 3, lane 3 and 4). The pDD-2 replication is dependent on two factors: the double-D sequence in-cis and REP gene products in-trans, because the cloning vector pGEM-3Z did not replicate under the same conditions and a plasmid containing only REP gene without CAP gene can also supply the helper function in trans for pDD-2 (data not shown).

Figure 4A:
FIG. 4. Comparison of replication of pDD-2 with psub201 and pSM620. Plasmid pDD-2 was cotransfected with equal amounts of either pAAV/Ad (lane 1), psub201 (lane 2) or pSM620 (lane 3) into Ad5 infected 293 cells. Low molecular weight DNA was extracted and digested with DpnI and analyzed on a 1% agarose gel. (A) Ethidium bromide staining. (B) Southern blot with an ITR oligonucleotide probe.
Figure 4B:
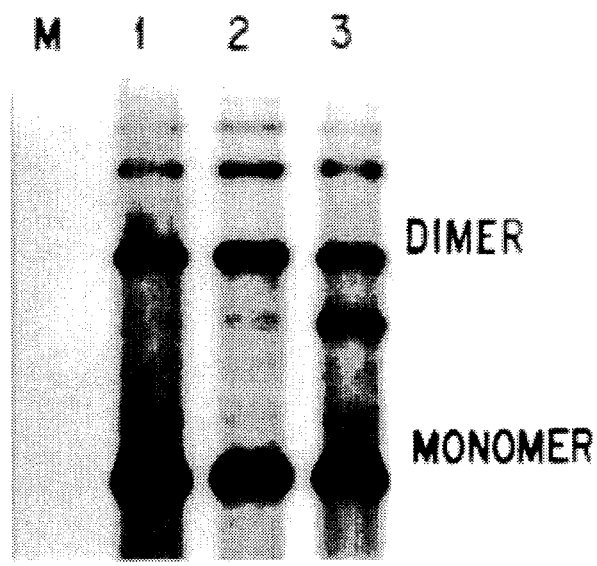

Since the replication of pDD-2 with one modified ITR was very efficient, a comparison was made between pDD-2 and two other infectious AAV plasmids, psub201 [Samulski, et. al., 1987. J. Virol, 61:3096– 3101.] and pSM620 [Samulski, et. al., 1982, Proc. Natl. Acad. Sci. U.S.A. 79:2077–2081.], which possesses two ITRs as well as wild type REP and CAP genes. The pDD- 2 was cotransfected into Ad5 infected cells with equal amounts of either pAAV/Ad helper (without ITR), psub201 or pSM620. The plasmid DNA was extracted 2 days post transfection, digested with DpnI, separated on 1% agarose gel. Southern blot was performed with an oligonucleotide probe from the A sequence of the ITR so that it can detect all the replicated DNA containing ITRs. As shown in FIG. 4, all three plasmids containing AAV coding genes can complement the pDD-2 replication equally well. However, psub201 itself replicated at a much lower level although it can complement pDD-2 replication effectively. pSM201 replicated at a similar level as pDD-2.

Figure 5A:
FIG. 5. Replication assay for double-D plasmids with different sizes. pDD-2 or pDD-neo were cotransfected with helper pAAV/Ad into Ad5 infected 293 cells, Low molecular weight DNA was extracted and digested with DpnI and analyzed on a 1% agarose gel. (A) Ethidium bromide staining. (B) Southern blot with $^{32}$P labeled plasmid pGEM 3Z probe.
Figure 5B:
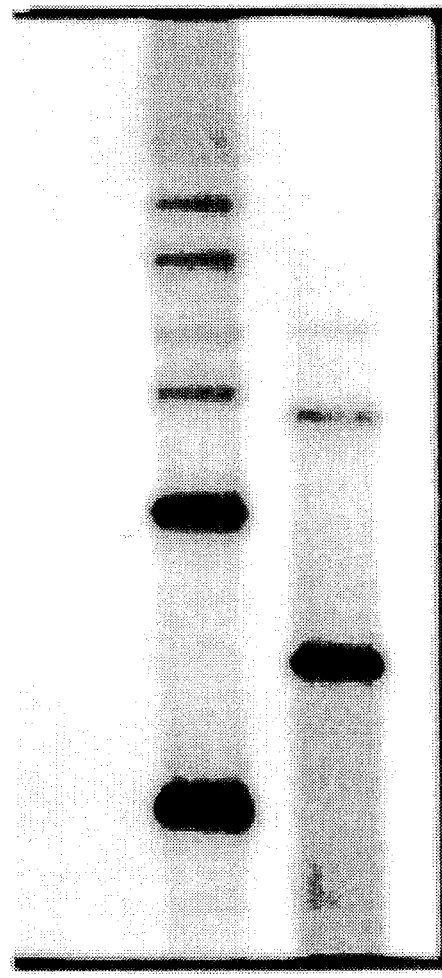

In order to determine whether the effectiveness of pDD-2 replication was due to the special double-D sequence or due to the smaller size of the plasmid (2.9 kb), a neo gene fragment of 1.2 kb was inserted into the SalI site at the polylinker of pDD- 2. The new plasmid pDD-neo is 4.1 kb in size, close to the size of wild type AAV (4.68 kb). This plasmid converted from a duplex circular to a linear molecule and replicated as efficiently as the parental pDD-2 (FIG. 5). Double-D plasmids were constructed with sizes up to 7.5 kb . These molecules also efficiently replicate (data not shown). The above results suggest that the double-D is an excellent substrate for Rep-dependent replication.

6.2.3. Replication and Rescue is Via AAV Mechanism

Figure 1C:
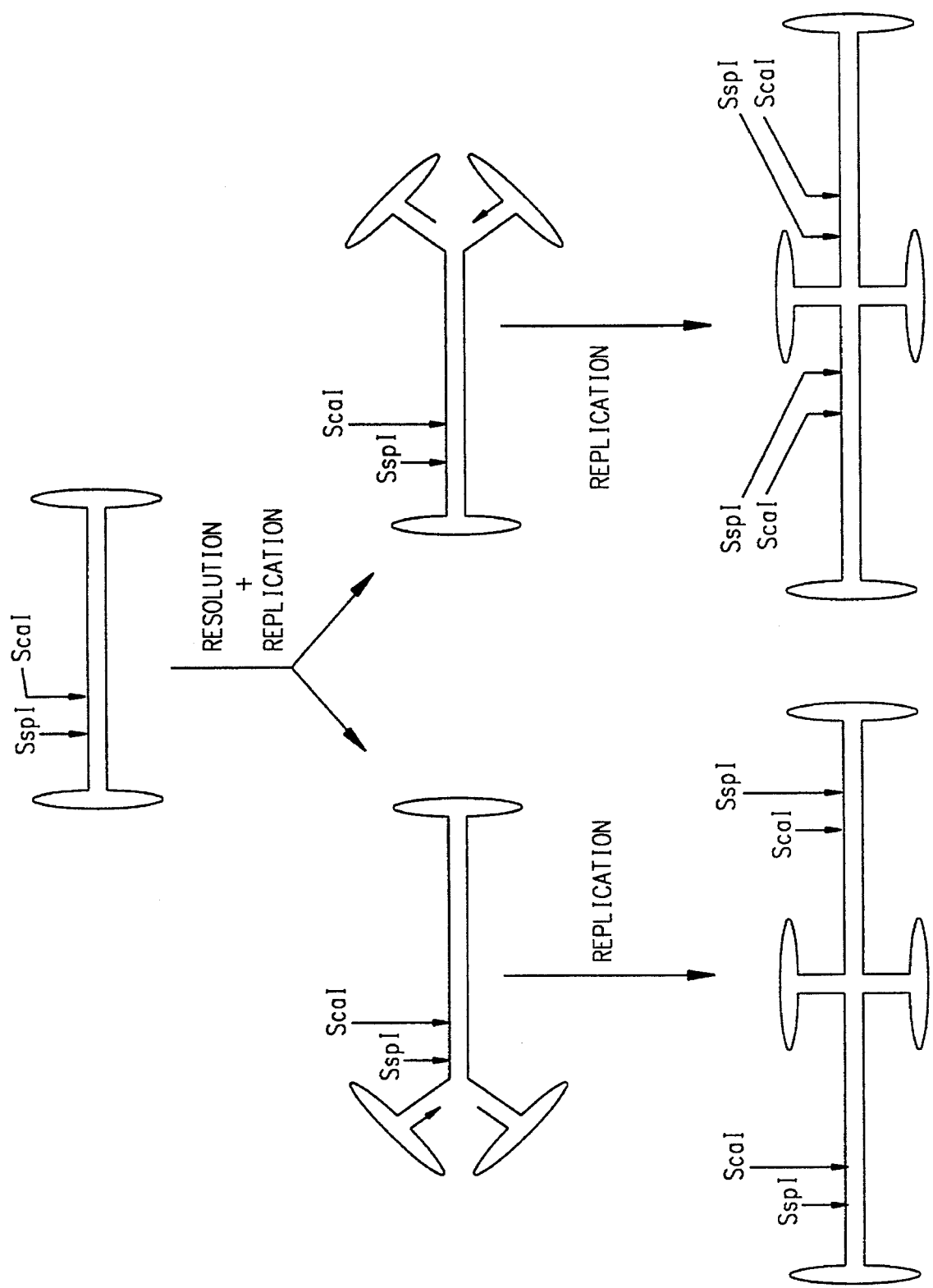

AAV inverted terminal repeats have been proven to be the viral replication origins. In vitro, these sequences are recognized as a substrate by REP protein, a site-and-strand-specific nickase and helicase. ITRs have also been considered as the substrate for AAV rescue [Muzyczka, N. 1992, Current Topics in Microbiology & Immunology. 158, 97–129]. Since the double-D plasmids contain one unique ITR and we have demonstrated that this sequence replicates only in the presence of REP proteins, it is attractive to predict that the rescue and replication are through similar AAV rescue and replication mechanisms (FIG. 1, A and B).

Figure 6:
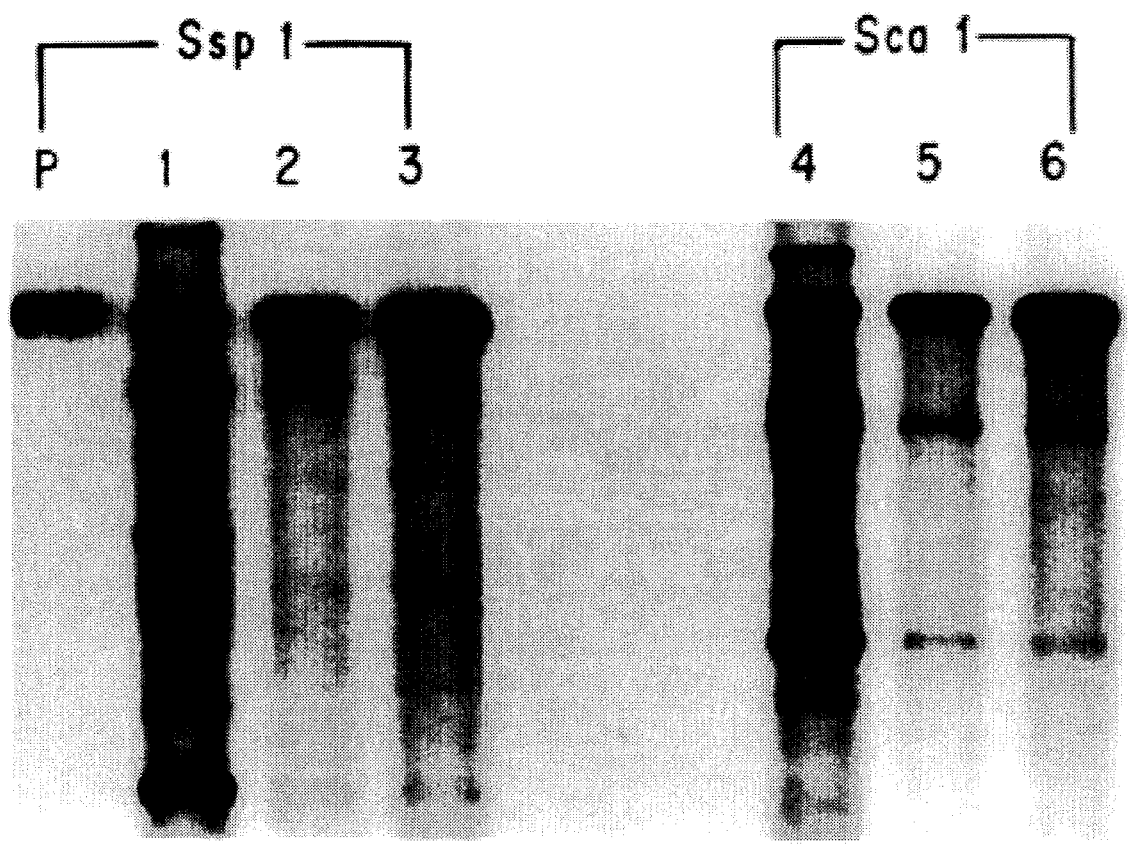
FIG. 6. Restriction analysis of rescue and replication of pDD-2. Plasmid pDD-2 was transfected into Ad5 infected or uninfected 293 cells with or without the cotransfection of helper plasmid pAAV/Ad. Low-molecular-weight DNA was digested with either SspI or ScaI and separated on a 1% agarose gel. Southern blot was done with a $^{32}$P labeled ITR probe.

In order to test the above assumption, pDD-2 DNA was transfected into Ad5 infected 293 cells with or without helper plasmid, or transfected into uninfected 293 cells. Subsequently, the plasmid DNA was subjected to restriction analysis by two single cutter enzymes SspI and ScaI respectively (for map, see FIG. 2). The DNA was probed with ITR oligonucleotide so that only the ITR-containing fragments would be detected. The results are shown in FIG. 6. After SspI or ScaI digestion, a linear full length plasmid band could be observed throughout all the lanes (P to 6). This band was derived from the unresolved input circular plasmid. While in lane 1 and 4 (Ad5 plus helper plasmid), four additional bands with expected molecular weight could also be seen. Two of them arose from internal head-to-head and tail-to-tail fragments of the digested dimer molecules. The other two bands are derived by digested monomer and dimer external fragments, most likely suggesting that pDD-2 is resolved at the unique double-D site and replicated via AAV replication scheme. It is noteworthy that in Ad5 infected cells (lane 2 and 5) and uninfected cells (lane 3 and 6), two fainter bands from the resolved monomer were also visible, suggesting that some cellular mechanism can initiate the rescue process at the double-D site in the absence of any other AAV sequence or AAV gene product. Although, such rescued DNA could not replicate in the absence of Rep proteins (see FIG. 3, lane 2) this suggests that the double D substrate may confer special features involved in the first step of AAV recognition not seen with the conviential AAV plasmids containing two wild type ITR's.

6.2.4. One DD-ITR IN-CIS is sufficient for AAV Viability

Since plasmids with a single modified DD-ITR could efficiently replicate like wild type AAV, the following questions were consequently asked: can this replicated DNA be encapsidated into virions. If so, can these virions infect cells and establish a latent infection by integration into cellular DNA. Finally, can these latent sequences be subsequently rescued out away from the chromosomes and re-enter the productive pathway upon superinfection with the wild type AAV and adenovirus.

In an effort to address the above questions, plasmid pDD-neo was used to generate the DD-neo virus preparation as described in Section 6.1.4. The cell lysates containing the recombinant virus particles were then used to infect human Detroit 6 cells. Two weeks post infection cells were selected against G418. A number of neo-resistant clones were isolated, indicating that the recombinant viruses were made and transduction was accomplished. DD-neor cell lines were superinfected with wild type AAV-2 and Ad5 and assayed for transduced DNA rescue and replication. Then the viral DNA was extracted and probed with a neogene fragment. Examples of DD-neor cell lines that rescued DD-neo viral DNA replicated as monomer and dimer (data not shown). These results demonstrated that the 165 bp single double-D is the only cis-sequence required to fulfill all the steps in AAV life cycle. Thus, the processes such as rescue from the plasmid, replication of the DNA, encapsidation of the virus, infection into the cells, integration into the chromosome and rescue back again were all mediated by this unique double-D sequence.

The present invention is not to be limited in scope by the exemplified embodiments disclosed herein which are intended as illustrations of single aspects of the invention, and any clones, DNA or amino acid sequences which are functionally equivalent are within the scope of the invention. Indeed, various modifications of the invention, in addition to those shown and described herein, will become apparent to those skilled in the art from the foregoing description and accompanying drawings. Such modifications are intended to fall within the scope of the appended claims.

It is also to be understood that all base pair and amino acid residue numbers and sizes given for nucleotides and peptides are approximate and used for the purposes of description.

Various publications are cited herein that are hereby incorporated by reference in their entireties.

What is claimed is:

1. A nucleic acid molecule comprising a 165 base pair nucleotide sequence as depicted in FIG. 9 (SEQ ID NO: 1).

2. A recombinant DNA vector comprising a DNA nucleotide sequence encoding a protein of interest and a 165 base pair nucleotide sequence as depicted in FIG. 9 (SEQ ID NO: 1).

3. The recombinant DNA vector according to claim 2 further comprising a DNA nucleotide sequence that encodes the AAV REP and CAP proteins.

4. The recombinant DNA vector according to claim 2 further comprising a DNA nucleotide sequence recognized by bacterial gamma delta resolvase as depicted in FIG. 10 (SEQ ID NO: 2).

5. The recombinant DNA vector according to claim 3 further comprising a DNA nucleotide sequence recognized by bacterial gamma delta resolvase as depicted in FIG. 10 (SEQ ID NO: 2).

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:1:

| | | | | | | |
|---|---|---|---|---|---|---|
| AGGAACCCCT | AGTGATGGAG | TTGGCCACTC | CCTCTCTGCG | CGCTCGCTCG | CTCACTGAGG | 60 |
| CCGGGCGACC | AAAGGTCGCC | CGACGCCCGG | GCTTTGCCCG | GGCGGCCTCA | GTGAGCGAGC | 120 |
| GAGCGCGCAG | AGAGGGAGTG | GCCAACTCCA | TCACTAGGGG | TTCCT | | 165 |

( 2 ) INFORMATION FOR SEQ ID NO:2:

( i ) SEQUENCE CHARACTERISTICS:
        ( A ) LENGTH: 120 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:2:

| | | | | | | |
|---|---|---|---|---|---|---|
| CCCTGTATCC | TAAATCAAAT | ATCGGACAAG | CAGTGTCTGT | TATAACAAAA | AATCGATTTA | 60 |
| ATAGACACAC | CAACAGCATG | GTTTTATGT | GTGCGATAAT | TTATAATATT | TCGGACAGGG | 120 |

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

GGAATTCAGG AACCCCTAGT GATGG        25

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:4:

TTGGCCACTC CCTCTCTGCG        20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:5:

AGGAACCCCT AGTGATGGAG        20

( 2 ) INFORMATION FOR SEQ ID NO:6:

( i ) SEQUENCE CHARACTERISTICS:
        ( A ) LENGTH: 145 base pairs
        ( B ) TYPE: nucleic acid
        ( C ) STRANDEDNESS: single
        ( D ) TOPOLOGY: unknown -continued ( i i ) MOLECULE TYPE: DNA (genomic)

( x i ) SEQUENCE DESCRIPTION: SEQ ID NO:6:

```
AGGAACCCCT  CGTGCTGGCG  TTGGCCACTC  CCTCTCTGCG  CGCTCGCTCG  CTCACTGAGG    60
CCGCCCGGGC  AAAGCCCGGG  CGTCGGGCGA  CCTTTGGTCG  CCCGGCCTCA  GTGAGCGAGC   120
GAGCGCGCAG  CGCGGGCGTG  GCCAA                                            145
```